(12) United States Patent
Klingenbeck

(10) Patent No.: US 8,644,448 B2
(45) Date of Patent: Feb. 4, 2014

(54) METHOD FOR COLLIMATING TO AN OFF-CENTER EXAMINATION SUB-OBJECT

(75) Inventor: Klaus Klingenbeck, Aufseβ (DE)

(73) Assignee: Siemens Aktiengesellschaft, Munich (DE)

(*) Notice: Subject to any disclaimer, the term of this patent is extended or adjusted under 35 U.S.C. 154(b) by 341 days.

(21) Appl. No.: 13/224,377

(22) Filed: Sep. 2, 2011

(65) Prior Publication Data

US 2012/0063565 A1 Mar. 15, 2012

(30) Foreign Application Priority Data

Sep. 15, 2010 (DE) .......................... 10 2010 040 812

(51) Int. Cl.
*A61B 6/00* (2006.01)
(52) U.S. Cl.
USPC .................................................. 378/9; 378/16
(58) Field of Classification Search
USPC ........................................ 378/4–20, 145–153
See application file for complete search history.

(56) References Cited

U.S. PATENT DOCUMENTS

2003/0076920 A1  4/2003  Shinno et al.

FOREIGN PATENT DOCUMENTS

DE  19802405 B4  8/1999
DE  102007014134 A1  9/2008

*Primary Examiner* — Courtney Thomas

(57) ABSTRACT

A method is proposed for collimating an off-center sub-object of an examination subject by a collimator of an X-ray diagnostic apparatus. The apparatus has a computed tomography imaging system having a first X-ray source and a computed tomography X-ray detector disposed opposite the first X-ray source having a number of individual detectors and an angiographic imaging system having a second X-ray source offset to the first X-ray source and a flat panel X-ray detector disposed opposite the second X-ray source with matrix shaped pixel elements. A 3D image of the subject is taken by the CT imaging system. The off-center sub-object is selected based on the 3D image. The position of the sub-object is determined for a shooting position of the angiographic imaging system according to the fixed relative disposition between the angiographic imaging system and the CT imaging system. The collimator is adjusted accordingly for collimating the off-center section.

7 Claims, 2 Drawing Sheets

METHOD FOR COLLIMATING TO AN OFF-CENTER EXAMINATION SUB-OBJECT

CROSS REFERENCE TO RELATED APPLICATIONS

This application claims priority of German application No. 10 2010 040 812.3 filed Sep. 15, 2010, which is incorporated by reference herein in its entirety.

FIELD OF THE INVENTION

The invention relates to a method for collimating to an off-center examination sub-object by means of an imaging system of an X-ray diagnostic apparatus having a rotatable gantry.

BACKGROUND OF THE INVENTION

X-ray diagnostic systems are standard medical imaging equipment and are used e.g. for interventional therapy. Angiographic systems, generally C-arm X-ray systems, are typically used for monitoring vascular and heart disease therapy and for minimally invasive tumor therapy. Their flat-panel X-ray detectors with pixel elements disposed in a matrix provide a very high local resolution (pixel size generally about 150 µm) and can be used for both for 2D and 3D imaging (Siemens DynaCT). In 3D imaging, however, the conventional CT machines are still superior in terms of low-contrast resolution and imaging speed; in 2D imaging, on other hand, they have disadvantages in terns of the resolution and scan field.

To utilize the advantages of both systems, an X-ray diagnostic apparatus is known e.g. from DE 198 02 405 B4 wherein two imaging systems are disposed on a rotating gantry, a CT imaging system with a line scan X-ray detector and an angiographic imaging system with a large area X-ray detector. With the CT imaging system, the known CT modalities can be implemented, e.g. the taking of sequential slices using so-called stop-and-shoot movement of a patient table or helical imaging with continuous movement of the patient table and continuous gantry rotation. With the angiographic imaging system, two known modalities can be implemented: 2D fluoroscopic imaging with stationary gantry and 3D rotational imaging (e.g. DynaCT) with continuously or sequentially rotating gantry.

SUMMARY OF THE INVENTION

The object of the present invention is to collimate to an off-center examination sub-object as precisely as possible by means of an angiographic imaging system in an X-ray diagnostic apparatus of this kind.

This object is achieved according to the invention by a method for collimating to an off-center examination sub-object by means of an imaging system of an X-ray diagnostic apparatus with a rotating gantry as claimed in the independent claim. Advantageous embodiments of the invention are set forth in the respective dependent claims.

The method according to the invention is carried out by means of an X-ray diagnostic apparatus with a rotating gantry, said X-ray diagnostic apparatus having two imaging systems disposed in the gantry, wherein a computed tomography imaging system has a first X-ray source and a computed tomography X-ray detector disposed opposite said first X-ray source and comprising an array of individual detectors, and a second imaging system, in particular an angiographic imaging system, having a second X-ray source which is offset to the first X-ray source, and a large area X-ray detector disposed opposite the second X-ray source and having pixel elements disposed in a matrix. The method according to the invention for collimating to an off-center sub-object of an examination subject by means of a collimator comprises the following steps:
a) Taking a 3D image of the examination subject by means of the CT imaging system,
b) Selecting the off-center examination sub-object on the basis of the 3D X-ray image,
c) Determining the collimator setting for collimating to the sub-object on the basis of the 3D image for a shooting position of the angiographic imaging system taking into account the fixed relationship between the angiographic imaging system and the CT imaging system and
d) Collimating to the off-center examination sub-object by adjusting the collimator.

In particular, in an additional step
e) an X-ray image of the sub-object is taken by the angiographic imaging system.

An advantage of the method according to the invention is that precise off-center collimation achieves a reduction in the radiation dose for the examination subject by avoiding unnecessary radiation. This is on the one hand more healthy for the patient and, on the other, can be used for more precise diagnosis. In addition, it eliminates time-consuming central positioning of the sub-object, necessitating the repositioning of the examination subject (the patient). Imaging now becomes possible in cases where the sub-object cannot be centrally positioned for anatomical reasons. The selective collimation can also reduce the radiation exposure for the physician as there is less stray radiation.

According to an embodiment of the invention, registration between the angiographic imaging system and the CT imaging system is carried out prior to the method.

The collimator advantageously has different elements, known as collimator jaws, and the collimator elements are individually controlled and positioned for collimation, thereby enabling particularly precise collimation to the sub-object.

According to another embodiment of the invention, the smallest image section which completely renders the sub-object is collimated to. This prevents portions of the sub-object from being truncated in the image, thereby losing important information; on the other hand, as little additional, unnecessary information as possible is acquired.

According to a first alternative, the collimation is carried out simply for a stationary angiographic imaging system. Any number of X-ray images can then be taken, as long as no movement of the gantry or examination subject takes place. This is particularly suitable for simple fluoroscopic operation of the X-ray diagnostic apparatus.

According to a second alternative, the angiographic imaging system rotates around the examination subject and the steps c) and d) and e) are repeated for each shooting position of the angiographic imaging system. In this embodiment, a 3D X-ray image can be produced by the angiographic imaging system from a large number of projection images taken at different shooting positions, the sub-object always being precisely collimated at each shooting position (i.e. at each projection angle).

BRIEF DESCRIPTION OF THE DRAWINGS

The invention and other advantageous embodiments, as set forth in features of the dependent claims, will now be explained in greater detail with reference to schematically illustrated examples in the accompanying drawings, said examples being illustrative of the invention but not to be taken in a limiting sense.

DETAILED DESCRIPTION OF THE INVENTION

Figure 1:
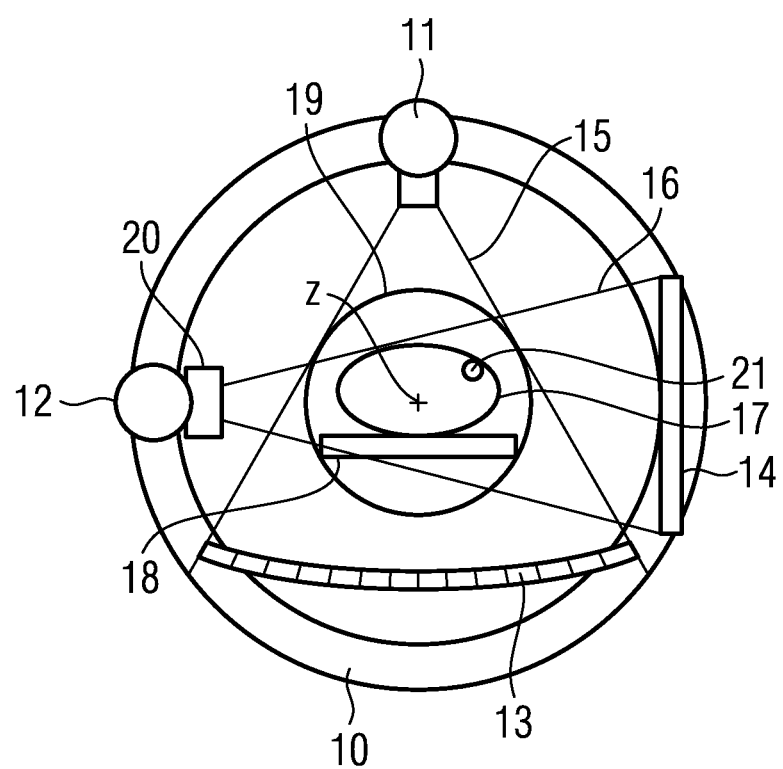
FIG. 1 shows a known X-ray diagnostic apparatus with two imaging systems.

A known X-ray diagnostic apparatus shown in FIG. 1 contains, in a gantry 10, a computed tomography (CT) imaging system with a first X-ray source 11 and a CT X-ray detector 13, and an angiographic imaging system with a second X-ray source 12 and a second flat panel X-ray detector 14. In the case of the CT imaging system, the first X-ray source 11 emits a fan beam 19 and the CT X-ray detector 13 is curved and composed of a number of individual detectors (e.g. 512). To scan an examination subject 17 disposed on a patient table 18, the CT imaging system rotates around the examination subject 17 through 360° by means of the gantry 10; the data set acquired can be reconstructed into a 3D volume image.

The angiographic imaging system has a second X-ray source 12 and a flat panel X-ray detector 14; the second X-ray source emits a conical X-ray beam 16 onto the flat panel X-ray detector 14. Between the first perpendicular bisector from the first X-ray source 11 onto the CT X-ray detector 13 and the second perpendicular bisector from the second X-ray source 12 onto the flat panel X-ray detector 14 an offset angle a exists which can be used to describe the offset between CT imaging system and angiographic imaging system. Said offset angle is preferably 90°. By means of the angiographic imaging system, 2D projection images can be taken with stationary gantry and a projection image data set reconstructable into a 3D image can be obtained with rotating gantry. The CT imaging system and the angiographic imaging system can be operated simultaneously or alternately, as described, for example, in DE 198 02 405 B4. For controlling the X-ray diagnostic apparatus, a system controller, for example, is provided which controls both the CT imaging system and the angiographic imaging system. Such a system controller can be constituted by a control PC.

Registration between a 3D volume image of the CT imaging system and a 2D projection image of the angiographic imaging system can take place e.g. as follows: the projection direction of a 2D projection image taken by the angiographic imaging system is determined relative to the 3D volume image taking into account the geometric disposition between CT imaging system and angiographic imaging system. As the geometric disposition between CT imaging system and angiographic imaging system on the gantry is fixed and known (offset angle a), the projection direction of the angiographic imaging system relative to the CT imaging system can be simply derived and the projection direction in the 3D volume image determined. A 2D projection image for the ascertained projection direction of the angiographic imaging system is then simulated, e.g. by means of a computational unit, from the 3D volume image or rather the data set from which the 3D volume image was reconstructed. Such 2D projection images simulated from CT data sets are known and are also termed DRR (Digitally Reconstructed Radiograph). The 2D projection image acquired by the angiographic scanning unit and the 2D projection image simulated for the same projection direction from the 3D data set are matched to one another e.g. by taking magnification factors into account. The acquired 2D projection image is then superimposed on the 3D volume image using the simulated 2D projection image; the superimposed images can optionally be displayed e.g. on a display unit of the X-ray diagnostic apparatus.

The X-ray diagnostic apparatus is designed to image off-center organs, i.e. sub-objects 21 of the examination subject 17 which are disposed some distance away from the isocenter Z and which also cannot be brought close to the isocenter by repositioning (e.g. liver in the case of interventional treatment of tumors or left atrium in the case of ablation of atrial fibrillation). By means of the method according to the invention, off-center collimation is possible, which has the advantage of minimizing the radiation exposure of the examination subject.

Figure 2:
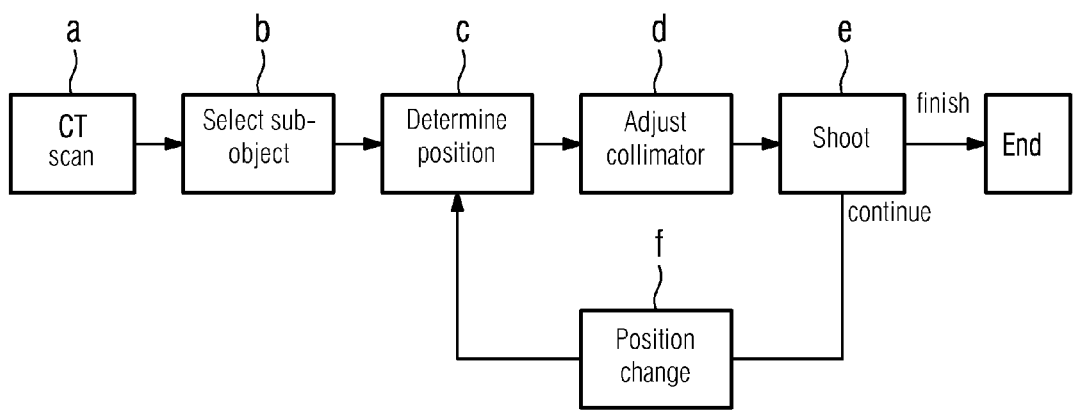
FIG. 2 shows a sequence of a method according to the invention.

The method according to the invention comprises the following steps which are shown in FIG. 2: in a first step a) a 3D image of the entire examination subject is produced by means of the CT imaging system. Because of the curved, elongated shape of the CT X-ray detector, the examination subject can be completely imaged by the CT imaging system. In a second step b), the off-center examination sub-object (i.e. the patient's organ, for example) to be imaged by means of the angiographic imaging system is selected on the basis of the 3D X-ray image of the CT imaging system. This can be done either automatically e.g. by the system controller or by means of segmentation or image recognition. Manual intervention by the user is also possible.

In a third step c, the collimator setting for collimating to the sub-object is then determined from the 3D image for a shooting position of the angiographic imaging system taking into account the fixed relative disposition between the angiographic imaging system and the CT imaging system. This can be performed e.g. by means of the system controller or a computational unit. The relative disposition between the angiographic imaging system and the CT imaging system, the shooting position of the angiographic imaging system, the sub-object to be collimated to in the 3D image and the collimator as well as its setting options are known to the X-ray diagnostic apparatus. This provides a simple means of calculating how the collimator elements of the collimator must be set and positioned in order to completely image the sub-object for the shooting position, it being preferably provided that the smallest possible image section which shows the sub-object in its entirety is collimated to, so that where possible no or few additional parts of the examination subject are targeted along with the sub-object. A shooting position of the angiographic imaging system is to be understood as meaning a particular fixed disposition of the angiographic imaging system relative to the examination subject. When the gantry is rotated around the examination subject, the angiographic imaging system consecutively assumes a plurality of shooting positions.

Figure 3:
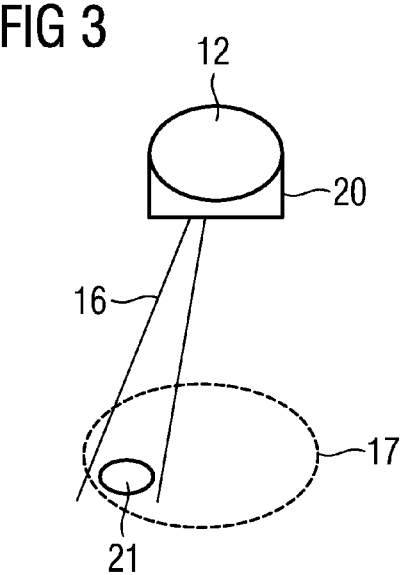
FIG. 3 shows collimation to an off-center examination sub-object.

In a fourth step d) the sub-object is collimated to by adjusting the collimator or more specifically the collimator elements. The adjustment of the collimator elements in accordance with the manner defined in step c) can be carried out automatically by the system controller, for example. FIG. 3 shows e.g. how the X-ray beam 16 is shaped by the collimator 20 such that it only collimates to and irradiates the off-center examination sub-object 21.

Then in a fifth step e), an X-ray image or a plurality of X-ray images can be taken in the shooting position of the angiographic imaging system. For the case that X-ray images are to be taken only in one shooting position of the angiographic imaging system, i.e. the gantry remains fixedly stationary, this completes the process. For the case that the gantry rotates and a plurality of X-ray images are to be taken by the angiographic imaging system and e.g. reconstructed into a 3D image, in a sixth step f) the shooting position of the angiographic imaging system is changed and the steps c) and d) and e) are repeated for a new shooting position of the angiographic imaging system. This can be repeated more than once or many times until the rotation is complete. Once shooting of the plurality of X-ray images in different shooting positions is complete, reconstruction of the X-ray images into 3D image can be carried out.

Prior to the method according to the invention, coarse adjustment of the collimator can be performed already for each shooting position of the angiographic imaging system by means of an X-ray image taken by the angiographic imaging system. For this purpose the collimator is positioned as centrally as possible above the examination subject and the collimator is minimized accordingly. However, since in an X-ray image of this kind virtually no soft tissue resolution is visible, additional information can be derived from the CT imaging system's 3D image taken in particular at low X-ray dose. From said CT 3D image, the position and extent of the sub-object can be precisely defined. As the CT imaging system and the angiographic imaging system are interconnected in a fixed manner, the relative geometry is known and the two systems are mutually registered. If a particular shooting position and magnification are now set for the angiographic imaging system, the sub-object can be adjusted accordingly in the CT 3D image and displayed as a virtual projection image, e.g. as a DRR. If the shooting position and/or the magnification changes, the adjustment can be repeated automatically. The information concerning the position and extent of the sub-object in the CT 3D image is communicated to the system controller which adjusts the collimator of the angiographic imaging system accordingly in each case.

The invention may be summarized as follows: for improved off-center collimation, a method is proposed for collimating to an off-center sub-object of an examination subject by means of a collimator of an imaging system of an X-ray diagnostic apparatus with a rotating gantry, said X-ray diagnostic apparatus having two imaging systems disposed in the gantry, wherein a computed tomography imaging system has a first X-ray source and a computed tomography X-ray detector disposed opposite the first X-ray source and comprising a number of individual detectors, and a second imaging system, in particular an angiographic imaging system, has a second X-ray source which is offset to the first X-ray source, and a flat panel X-ray detector disposed opposite the second X-ray source with pixel elements disposed in matrix shaped manner, comprising the following steps:
a) Taking of an 3D image of the examination subject by means of the CT imaging system,
b) Selecting the off-center examination sub-object on the basis of the 3D X-ray image,
c) Determining the position of the off-center examination sub-object on the basis of the 3D image for a shooting position of the angiographic imaging system taking into account the fixed relative disposition between the angiographic imaging system and the CT imaging system, and
d) Collimating to the eccentrically disposed section by adjusting the collimator.

The invention claimed is:

1. A method for collimating an off-center sub-object of an examination subject by a collimator of an imaging system of an X-ray diagnostic apparatus with a rotating gantry, comprising:
  disposing a computed tomography imaging system in the rotating gantry comprising a first X-ray source and a computed tomography X-ray detector disposed opposite the first X-ray source and comprising an array of individual detectors;
  disposing an angiographic imaging system comprising a second X-ray source offset to the first X-ray source, and a flat panel X-ray detector disposed opposite the second X-ray source and comprising a matrix-shaped pixel elements;
  taking a 3D X-ray image of the examination subject by the computed tomography imaging system;
  selecting the off-center examination sub-object based on the 3D X-ray image;
  determining a collimator setting for a shooting position of the angiographic imaging system based on a fixed relative disposition between the angiographic imaging system and the computed tomography imaging system; and
  collimating the off-center examination sub-object by adjusting the collimator according to the collimator setting.

2. The method as claimed in claim 1, further comprising taking an X-ray image of the sub-object by the angiographic imaging system.

3. The method as claimed in claim 1, wherein the angiographic imaging system and the computed tomography imaging system are registered with each other prior to carrying out the method.

4. The method as claimed in claim 1, wherein the collimator comprises a plurality of elements and the collimator elements are individually controlled and positioned for collimation.

5. The method as claimed in claim 1, wherein a smallest image section that completely renders the sub-object is collimated to.

6. The method as claimed in claim 1, wherein the angiographic imaging system is a stationary angiographic imaging system.

7. The method as claimed in claim 1, wherein the angiographic imaging system is rotated around the examination subject, and wherein the collimator setting is determined for each shooting position of the angiographic imaging system and the collimator is adjusted accordingly.

* * * * *